(12) United States Patent
Narasimhan et al.

(10) Patent No.: US 7,232,466 B2
(45) Date of Patent: Jun. 19, 2007

(54) METHOD AND COMPOSITIONS FOR PROVIDING NATURAL APPEARING HAIR COLOR

(75) Inventors: Saroja Narasimhan, Matawan, NJ (US); Lou Ann Christine Vena, Scotch Plains, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 215 days.

(21) Appl. No.: 10/360,699

(22) Filed: Feb. 6, 2003

(65) Prior Publication Data

US 2004/0154108 A1   Aug. 12, 2004

(51) Int. Cl.
*A61K 7/13* (2006.01)
(52) U.S. Cl. .................... 8/405; 8/410; 8/411; 8/412; 8/424; 132/202; 132/208; 424/70.1
(58) Field of Classification Search ............. 132/202, 132/208; 424/70.1; 8/405, 410, 411, 412, 8/424
See application file for complete search history.

(56) References Cited

U.S. PATENT DOCUMENTS

| | | |
|---|---|---|
| 924,048 A | 6/1909 | Ensor |
| 1,635,176 A | 7/1927 | Dorment |
| 1,876,033 A | 9/1932 | Starr |
| 2,031,774 A | 2/1936 | Helfrich .................. 132/13 |
| 2,397,321 A | 3/1946 | Leach ..................... 132/13 |
| 2,446,398 A | 8/1948 | Wilson .................... 132/13 |
| 2,755,807 A | 7/1956 | Jorgensen ................ 132/116 |
| 2,897,826 A | 8/1959 | Di Vito ................... 132/114 |
| 2,956,570 A | 10/1960 | Stanford ................. 132/116 |
| 3,059,652 A | 10/1962 | Thomas .................. 132/112 |
| 3,446,216 A | 5/1969 | Sala ...................... 132/116 |
| 3,456,658 A | 7/1969 | Long, Jr. ................ 132/116 |
| 3,912,446 A | 10/1975 | Zviak ..................... 8/10.1 |
| 3,961,635 A | 6/1976 | Miya ..................... 132/11 |
| 4,511,360 A * | 4/1985 | Monnais et al. ............ 8/405 |
| 4,516,591 A | 5/1985 | Hierholzer ............... 132/88.7 |
| 4,775,527 A | 10/1988 | Bires ..................... 424/62 |
| 4,813,439 A | 3/1989 | Morgan .................. 132/116 |
| 4,834,767 A | 5/1989 | Helioff ................... 8/416 |
| 4,957,731 A | 9/1990 | Helioff ................... 424/62 |
| 4,987,909 A | 1/1991 | Snyder ................... 132/202 |
| 5,024,243 A | 6/1991 | Snyder ................... 132/116 |
| 5,089,257 A | 2/1992 | Schrader ................. 424/70 |
| 5,224,964 A | 7/1993 | Shami .................... 8/405 |
| 5,422,031 A | 6/1995 | Nomura ................ 252/174.17 |

(Continued)

FOREIGN PATENT DOCUMENTS

DE   3931111 A1   9/1989

(Continued)

OTHER PUBLICATIONS

English abstract of the Patent DE 19713696 C1.*

(Continued)

*Primary Examiner*—Eisa Elhilo
(74) *Attorney, Agent, or Firm*—Julie Blackburn

(57) ABSTRACT

A method for improving the dimensionality and fade resistance of oxidatively colored or lightened hair, a method for oxidatively coloring or lightening hair, a kit for use in practicing the method, and the related compositions.

24 Claims, 1 Drawing Sheet

U.S. PATENT DOCUMENTS

| | | | | |
|---|---|---|---|---|
| 5,560,750 A | 10/1996 | Crews | | 8/431 |
| 5,575,989 A | 11/1996 | Caskey | | 424/62 |
| 5,635,461 A | 6/1997 | Onitsuka | | 510/126 |
| 5,674,476 A | 10/1997 | Clausen | | 424/62 |
| 5,688,291 A | 11/1997 | Said | | 8/431 |
| 5,725,600 A | 3/1998 | Caisey | | 8/103 |
| 5,738,121 A | 4/1998 | Westerveld | | 132/113 |
| 5,843,193 A | 12/1998 | Hawkins | | 8/405 |
| 5,891,423 A | 4/1999 | Weeks | | 424/62 |
| 5,980,587 A | 11/1999 | Samain | | 8/426 |
| 5,989,530 A | 11/1999 | Lorenz | | 424/62 |
| 6,112,751 A | 9/2000 | Bennett | | 132/116 |
| 6,206,935 B1 | 3/2001 | Onitsuka | | 8/431 |
| 6,286,518 B1 | 9/2001 | Laporte | | 132/116 |
| 6,383,231 B1 | 5/2002 | Lang | | 8/405 |
| 6,440,177 B1 | 8/2002 | Orr | | 8/426 |
| 6,453,909 B1 | 9/2002 | Delaforcade | | 132/208 |
| 6,457,476 B1 | 10/2002 | Elmer | | 132/114 |
| 6,596,035 B2 | 7/2003 | Gutkowski | | 8/405 |
| 6,835,018 B2 | 12/2004 | Miczewski | | 401/196 |
| 2003/0154562 A1 | 8/2003 | Sarojini | | 8/405 |
| 2004/0016064 A1 | 1/2004 | Vena | | 8/406 |

FOREIGN PATENT DOCUMENTS

| | | | |
|---|---|---|---|
| DE | 19713696 C1 | * | 6/1998 |
| JP | 411018822 A | | 1/1999 |
| JP | 411137329 A | | 5/1999 |
| JP | 02001046140 A | | 2/2001 |

OTHER PUBLICATIONS

Zviak, Charles. The Science of Hair Care, Marcel Dekker, Inc., pp. 214-277.

wwwglobalcosmetic.com (GCI), Sep. 2002, pp. 61 and 62.

Maxim, Permanent Haircolor for Men, circa Jan. 1, 2000.

L'Oreal Feria, Colour Strands, Quick Shimmer Bleach Blasé C90, circa Jan. 1, 2000.

* cited by examiner

METHOD AND COMPOSITIONS FOR PROVIDING NATURAL APPEARING HAIR COLOR

TECHNICAL FIELD

The invention is in the field of methods and compositions for oxidatively coloring or lightening hair.

BACKGROUND OF THE INVENTION

In spite of the progress that has been made in formulating better oxidative, or permanent, hair color, one problem still remains. In particular, oxidatively colored hair exhibits a certain monochromatic color that is especially evident in certain shades. While an individual's natural, virgin hair may have one overall color, when one closely studies the hair strands it is seen that the individual strands exhibit considerable variability in color. It is that variability that provides what hair colorists refer to as "dimensionality". It is dimensionality that gives natural virgin hair its natural look.

While dimensionality can be achieved with high priced salon techniques, it is not readily obtainable with the retail hair coloring kits that are used by the majority of consumers. Accordingly, there is a need for retail, at-home hair color kits that provide dimensional oxidative color to hair.

It is an object of the invention to provide a method for providing dimensionality to oxidatively colored hair.

It is a further object of the invention to provide a kit containing the various components required to dimensional oxidatively color hair.

It is a further object of the invention to provide compositions for use in oxidatively coloring hair to provide dimensional hair color.

It is a further object of the invention to provide hair color compositions that provide improved fade resistance and/or color retention on the hair fibers.

SUMMARY OF THE INVENTION

A method for improving the dimensionality of oxidatively colored or lightened hair by post-treating the oxidatively colored or lightened hair with a post-treatment composition containing a dyestuff component but being free of any oxidizing agent reactive with said dyestuff component to form color.

A method for oxidatively coloring the hair comprising the steps of:

(a) treating the hair with an oxidative dye composition comprising at least one dyestuff component and at least one oxidizing agent reactive with the dyestuff component to form color, for a period of time sufficient to color the hair, (b) removing the oxidative dye composition from the hair but leaving residual oxidizing agent on at least portion thereof, (c) treating the hair with a post-treatment composition comprising at least one dyestuff component but being free of any oxidizing agent reactive with said dyestuff component to form color, whereby the dyestuff component in the post-treatment composition reacts with any residual oxidizing agent present on the hair to form color.

A method for lightening or providing color to hair comprising the steps of:

(a) treating the hair with a composition free of dyestuff components, comprising at least one oxidizing agent reactive with such dyestuff components to form color, for a period of time sufficient to color and/or lighten the hair, (b) removing the composition from the hair but leaving residual oxidizing agent on at least portion thereof, (c) treating the hair with a post-treatment composition comprising at least one dyestuff component but being free of any oxidizing agent reactive with said dyestuff component to form color, whereby the dyestuff component in the post-treatment composition reacts with any residual oxidizing agent present on the hair to lighten or color the hair.

A hair color kit comprising a storage receptacle having contained therein a first container containing an composition comprising a dyestuff component, a second container containing an oxidizing agent composition, and a third container containing a post-treatment composition comprising at least one dyestuff component but being free of any oxidizing agent reactive with said dyestuff component to form color.

A hair color kit comprising a storage receptacle having contained therein a first container containing a composition free of dyestuff components, a second container containing an oxidizing agent composition, and a third container containing a post-treatment composition comprising at least one dyestuff component but being free of any oxidizing agent reactive with said dyestuff component to form color.

BRIEF DESCRIPTION OF THE DRAWINGS

FIG. 2: is a container that contains the developer composition.

FIG. 3: is a container that contains the oxidative dye composition or the composition free of dyestuff components.

FIG. 4: is a container that contains the post-treatment composition.

FIG. 5: is a container that contains the optional hair conditioner composition.

DETAILED DESCRIPTION

I. The Method

Figure 1:
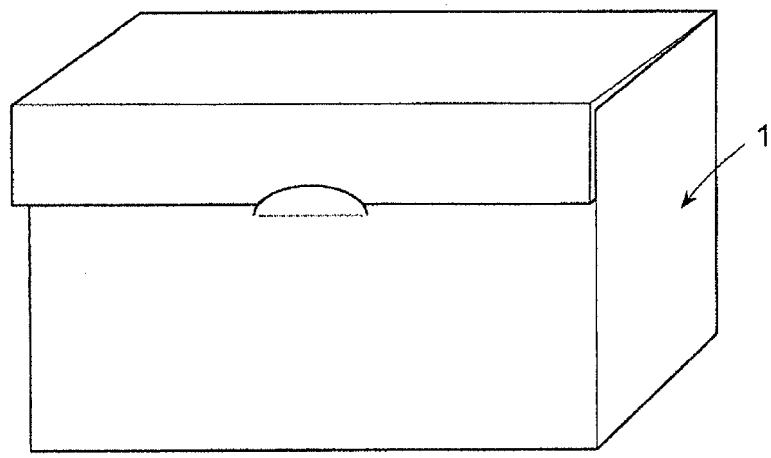
FIG. 1: illustrates the kit of the invention.

The invention comprises both a method for oxidatively coloring or lightening the hair and a method for improving the dimensionality of hair that has been oxidatively colored or lightened. In one embodiment, the hair is first dyed with oxidative color for a period of time sufficient to color the hair. The oxidative color is then removed, preferably by rinsing with water. The post-treatment composition is then applied to the hair and removed from the hair, preferably by rinsing with water. If desired the treated hair may be further treated by applying either a rinse-out or leave-in hair conditioner. In another embodiment, the composition initially combined with the oxidizing agent and applied to hair contains no dyestuff components. This occurs when it is desired to lighten the natural hair shade. The mixture of the composition and the oxidizing agent composition is applied to hair for the desired period of time, then rinsed off with water. The post-treatment composition is applied as noted above.

A. Coloring the Hair with the Oxidative Dye Composition

The hair is first colored with the oxidative dye composition in the usual manner. Any oxidative dye compositions are suitable, so long as they have sufficient oxidative dyestuff components to cause coloration of hair when the oxidative dye composition is combined with the developer, or oxidizing agent composition.

1. The Oxidative Dye Composition

In general, the oxidative dye compositions used in the method are aqueous based and comprise about 0–20%, preferably about 0.001–10%, more preferably about 0.01–8% by weight of the total oxidative dye composition of dyestuff components and about 0.0001–99.9%, preferably about 0.001–98%, more preferably about 0.001–90% by weight of the total composition of water base.

As noted above, it is possible for the oxidative dye composition to contain no dyestuff components, in the case where it is desired for the composition to simply lighten the base hair shade, followed by treatment with the post-treatment composition to the desired tones. In this case the dyestuff components are simply removed from the composition, which remains the same in other respects.

(a). Dyestuff Components

Dyestuff components include primary intermediates and, optionally, couplers for the formation of oxidation dyes.

Suggested ranges of primary intermediates present in the oxidative dye composition range from about 0–6%, preferably about 0.0001–5.5%, more preferably about 0.001–5% by weight of the total composition. Such primary intermediates are well known for use in hair color, and include ortho or para substituted aminophenols or phenylenediamines, such as para-phenylenediamines of the formula:

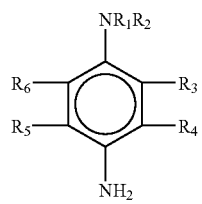

wherein $R_1$ and $R_2$ are each independently hydrogen, $C_{1-6}$ alkyl, or $C_{1-6}$ alkyl substituted with one or more hydroxy, methoxy, methylsulphonylamino, aminocarbonyl, furfuryl, unsubstituted phenyl, or amino substituted phenyl groups; $R_3$, $R_4$, $R_5$, and $R_6$ are each independently hydrogen, $C_{1-6}$ alkyl, $C_{1-6}$ alkoxy, halogen, or $C_{1-6}$ alkyl substituted with one or more hydroxy or amino groups.

Specific examples of suitable primary intermediates include para-phenylenediamine, 2-methyl-1,4-diaminobenzene, 2,6-dimethyl-1,4-diaminobenzene, 2,5-dimethyl-1,4-diaminobenzene, 2,3-dimethyl-1,4-diaminobenzene, 2-chloro-1,4-diaminobenzene, 2-methoxy-1,4-diaminobenzene, 1-phenylamino-4-aminobenzene, 1-dimethylamino-4-aminobenzene, 1-diethylamino-4-aminobenzene, 1-bis(beta-hydroxyethyl)amino-4-aminobenzene, 1-methoxyethylamino-4-aminobenzene, 2-hydroxymethyl-1,4-diaminobenzene, 2-hydroxyethyl-1,4-diaminobenzene, 2-isopropyl-1,4-diaminobenzene, 1-hydroxypropylamino-4-aminobenzene, 2,6-dimethyl-3-methoxy-1,4-diaminobenzene, 1-amino-4-hydroxybenzene, and derivatives thereof, and acid or basic salts thereof.

Preferred primary intermediates are p-phenylenediamine, p-aminophenol, o-aminophenol, N,N-bis(2-hydroxyethyl)-p-phenylenediamine, 2,5-diaminotoluene, their salts and mixtures thereof.

Suitable color couplers, if present, range from about 0.0001–10%, more preferably about 0.0005–8%, most preferably about 0.001–7% by weight of the total oxidative dye composition. Such color couplers include, for example, those having the general formula:

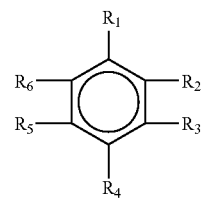

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, catechol, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methyl pyrazolone, 3,4-methylenedioxyphenol, 3,4-methylenedioxy-1-[(beta-hydroxyethyl)amino]benzene, 1-methoxy-2-amino-4-[(beta-hydroxyethyl)amino] benzene, 1-hydroxy-3-(dimethylamino)benzene, 6-methyl-1-hydroxy-3[(beta-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamionphenoxyethanol, and mixtures thereof.

Preferred couplers include resorcinol, 1-naphthol, 2-methylresorcinol, 4-amino-2-hydroxy toluene, m-aminophenol, 2,4-diaminophenoxyethanol, phenyl methyl pyrazolone, their salts, or mixtures.

In the haircolor industry, haircolor is classified into one of ten levels as follows:
1=very black
2=bright black
3=very dark brown
4=dark brown
5=medium brown
6=light brown
7=dark blonde
9=light blonde
10=high lift blonde Set forth in the table below is a non-limiting example of the primary intermediates and the color couplers that may be used in various shades of hair color. Other primary intermediates and couplers may be used in addition to, or in lieu of, those set forth in the Table and nothing herein shall be construed to limit the invention to only those primary intermediates and couplers set forth.

| Primary Intermediates | Couplers | Primary Intermediates | Couplers |
|---|---|---|---|
| Level 1 - Very Black | | Level 2 - Bright Black | |
| p-phenylenediamine | m-aminophenol | p-phenylenediamine | resorcinol |
| p-phenylenediamine sulfate | resorcinol | 2-chloro-P-phenylenediamine sulfate | |
| 2-chloro-phenylenediamine sulfate | 4-amino-2-hydroxytoluene | o-aminophenol | |
| p-aminophenol | 4-chlororesorcinol | | |
| o-aminophenol | m-aminophenol HCL | | |
| | 2,4-diaminophenoxy ethanol | | |
| | m-phenylenediamine sulfate | | |
| Level 3 - Very Dark Brown | | Level 4 - Dark Brown | |
| p-phenylenediamine | resorcinol | p-phenylenediamine | resorcinol |
| N,N-bis(2-hydroxyethyl)-P-phenylenediamine sulfate | 1-naphthol | N,N-bis(2-hydroxyethyl)-P-phenylenediamine sulfate | 1-naphthol |
| | m-aminophenol | p-aminophenol | m-aminophenol phenyl methyl pyrazolone |
| | | o-aminophenol | 4-amino-2-hydroxytoluene |
| Level 5 - Medium Brown | | Level 6 - Light Brown | |
| p-phenylenediamine | resorcinol | p-phenylenediamine | resorcinol |
| N,N-bis(2-hydroxyethyl)-P-phenylenediamine sulfate | 1-naphthol | N,N-bis(2-hydroxyethyl)-P-phenylenediamine sulfate | 1-naphthol |
| p-aminophenol | m-aminophenol | p-aminophenol | m-aminophenol |
| o-aminophenol | phenyl methyl pyrazolone | | phenyl methyl pyrazolone |
| | 2-methylresorcinol | | 4-amino-2-hydroxytoluene |
| | 4-amino-2-hydroxtoluene | | 2-methylresorcinol |
| Level 7 - Dark Blonde | | Level 8 - Medium Blonde | |
| p-phenylenediamine | resorcinol | p-phenylenediamine | resorcinol |
| N,N-bis(2-hydroxyethyl)-P-phenylenediamine sulfate | 1-naphthol | N,N-bis(2-hydroxyethyl)-P-phenylenediamine sulfate | 1-naphthol |
| p-aminophenol | phenyl methyl pyrazolone | p-aminophenol | m-aminophenol |
| o-aminophenol | | | phenyl methyl pyrazolone |
| | | | 4-amino-2-hydroxytoluene |
| Level 9 - Light Blonde | | Level 10 - High Lift Blonde | |
| p-phenylenediamine | resorcinol | p-phenylenediamine | resorcinol |
| N,N-bis(2-hydroxyethyl)-P-phenylenediamine sulfate | 4-amino-2-hydroxytoluene | N,N-bis(2-hydroxyethyl)-P-phenylenediamine sulfate | 1-naphthol |
| p-aminophenol | phenyl methyl pyrazolone | | phenyl methyl pyrazolone |
| o-aminophenol | 2-methylresorcinol | | 2-methylresorcinol |
| | 1-naphthol | | |

(b). Alkalizing Agent

The oxidative dye composition may also contain one or more alkalizing agents preferably in a range of about 0.1–5% based on the total weight of the oxidative dye composition. The term "alkalizing agent" means an ingredient that is capable of imparting alkalinity (e.g. a pH of greater than 7) to the dye mixture. Suitable alkalizing agents include ammonium hydroxide, metal hydroxides, alkanolamines, sodium silicate, metal carbonates, sodium metasilicate, and mixtures thereof. Suitable metal hydroxides and carbonates include alkali metal and alkaline earth metal hydroxides or carbonates. Examples of such metal hydroxides include sodium, potassium, lithium, calcium, magnesium and so on. A particularly preferred alkaline earth metal hydroxide is sodium hydroxide. Suitable alkanolamines include mono-, di-, and trialkanolamines such as monoethanolamine (MEA), diethanolamine (DEA), triethanolamine (TEA), 2-aminobutanol, aminoethyl propanediol, aminomethyl propanediol, bis-hydroxyethyl tromethamine, diethanolamine, diethyl ethanolamine, diisopropanolamine, dimethylamino methylpropanol, dimethyl MEA, isopropanolamine, methylethanolamine, mixed isopropanolamines, triisopropanolamine, tromethamine, and mixtures thereof. A particularly preferred alkanolamine is MEA.

The alkalizing agent present in the hair dye mixture may react with other ingredients in the mixture in situ, such as fatty acids, proteins or hydrolyzed proteins, and the like. Depending on the amount of alkalizing agent present and the presence or absence of ingredients that will react with the alkalizing agent, it is possible that the alkalizing agent may be completely reacted in situ, partially reacted in situ, or not reacted at all if there are no other ingredients in the composition that will react with the alkalizing agent. Most preferred is where the oxidative dye composition comprises mixtures of alkalizing agents, in particular, ammonium hydroxide in combination with a second alkalizing agent such as an alkanolamine.

(c). Other Ingredients (i) Fatty Acids

The composition may contain one or more fatty acids, and if so suggested ranges are about 0.001–15%, preferably 0.005–10%, most preferably 0.01–8% by weight of the total composition. If fatty acids are present they will react with the alkalizing agent to form soap in situ, which provides a more shampoo-like character to the aqueous hair color composition once it is applied to hair. Such fatty acids are of the general formula RCOOH wherein R is a straight or branched chain, saturated or unsaturated $C_{6-30}$ alkyl. Examples of suitable fatty acids include oleic acid, stearic acid, myristic acid, linoleic acid, and so on. Particularly preferred is oleic acid.

(ii) Conditioners

The oxidative dye composition may comprise one or more conditioners that exert a conditioning effect on hair. A variety of conditioners are suitable including cationic polymers, oily conditioning agents, fatty alcohols, proteins, and so on. A combined total weight of conditioners preferably ranges from about 0.1–25%, preferably 0.5–20%, more preferably 1–15% by weight of the total composition.

Cationic Polymers

A variety of cationic polymers are suitable as conditioners, such as quaternary derivatives of cellulose ethers or guar derivatives, copolymers of vinylpyrrolidone, polymers of dimethyldiallyl ammonium chloride, acrylic or methacrylic polymers, quaternary ammonium polymers, and the like.

Quaternary Derivatives of Cellulose

Examples of quaternary derivatives of cellulose ethers are polymers sold under the tradename JR-125, JR-400, JR-30M. Suitable guar derivatives include guar hydroxypropyl trimonium chloride.

Copolymers of Vinylpyrrolidone

Copolymers of vinylpyrrolidone having monomer units of the formula:

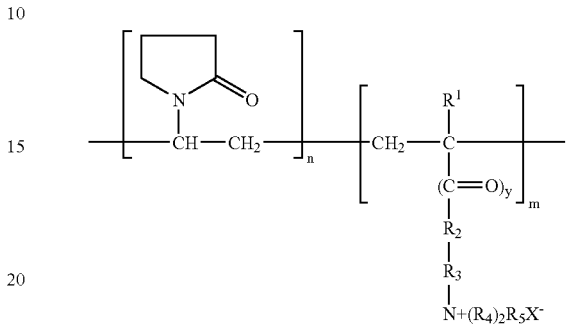

wherein $R^1$ is hydrogen or methyl, preferably methyl;
y is 0 or 1, preferably 1
$R^2$ is O or NH, preferably NH;
$R^3$ is $C_xH_{2x}$ where x is 2 to 18, or —$CH_2$—CHOH—$CH_2$, preferably $C_xH_{2x}$ where x is 2;
$R^4$ is methyl, ethyl, phenyl, or $C_{1-4}$ substituted phenyl, preferably methyl; and
$R^5$ is methyl or ethyl, preferably methyl.

Polymers of Dimethyldiallylammonium Chloride

Homopolymers of dimethyldiallylammonium chloride, or copolymers of dimethyldiallylammonium chloride and acrylamide are also suitable conditioners. Such compounds are sold under the tradename MERQUAT by Calgon.

Acrylic or Methacrylic Acid Polymers

Homopolymers or copolymers derived from acrylic or methacrylic acid, selected from monomer units acrylamide, methylacrylamide, diacetone-acrylamide, acrylamide or methacrylamide substituted on the nitrogen by lower alkyl, alkyl esters of acrylic acid and methacrylic acid, vinylpyrrolidone, or vinyl esters are suitable for use as conditioners.

Polymeric Quaternary Ammonium Salts

Suitable conditioners also include polymeric quaternary ammonium polymers such as Polyquaternium 10, 28 31, 33, 34, 35, 36, 37, and 39.

Diquaternary Polydimethylsiloxanes

Also suitable are diquaternary polydimethylsiloxanes such as Quaternium-80, sold by Goldschmidt Corporation under the tradename ABIL-Quat 3272.

Examples of other cationic polymers that can be used in the compositions of the invention are disclosed in U.S. Pat. Nos. 5,240,450 and 5,573,709, which are hereby incorporated by reference.

Particularly preferred are conditioners Polyquaternium 10 and Polyquaternium 28. Polyquaternium-10 is the polymeric quaternary ammonium salt of hydroxyethyl cellulose reacted with trimethyl ammonium substituted epoxide. Polyquaternium-28 is the polymeric quaternary ammonium salt consisting of vinyl pyrrolidone and dimethylaminopropyl methacrylamide monomers.

Oily Conditioning Agents

Also suitable are a variety of oily materials that provide good conditioning effect to hair. Suitable oils are liquid at room temperature and may comprise esters, hydrocarbons, and the like. Preferably the composition comprises 0.001–20%, more preferably 0.005–15%, most preferably 0.01–10% by weight of the total composition of such oils. Particularly preferred oily conditioning agents are oils extracted from vegetable sources, specifically meadowfoam seed oil.

(iii) Surfactants or Emulsifiers

The oxidative dye composition of the invention preferably comprises one or more surfactants that assist in maintaining the composition in the preferred emulsion form and aid in the foaming capability of the composition. Suitable surfactants include anionic surfactants, nonionic surfactants, amphoteric surfactants, and the like.

Nonionic Surfactants

Suggested ranges of nonionic surfactant, if present, are about 0.01–10%, preferably about 0.05–8%, more preferably about 0.1–7% by weight of the total composition. Suitable nonionic surfactants include alkoxylated alcohols or ethers, alkoxylated carboxylic acids, sorbitan derivatives, and the like.

Suitable alkoxylated alcohols, or ethers, are formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include steareth 2–30, which is formed by the reaction of stearyl alcohol and ethylene oxide where the number of repeating ethylene oxide units is 2 to 30; Oleth 2–30 which is formed by the reaction of oleyl alcohol and ethylene oxide where the number of repeating ethylene oxide units is 2 to 30; Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, and so on. Particularly preferred are Steareth-21, which is the reaction product of a mixture of stearyl alcohol with ethylene oxide, and the number of repeating ethylene oxide units in the molecule is 21, and Oleth-20 which is the reaction product of oleyl alcohol and ethylene oxide wherein the number of repeating ethylene oxide units in the molecule is 20.

Also suitable as the nonionic surfactant are alkyoxylated carboxylic acids, which are formed by the reaction of a carboxylic acid with an alkylene oxide or with a polymeric ether. The resulting products have the general formula:

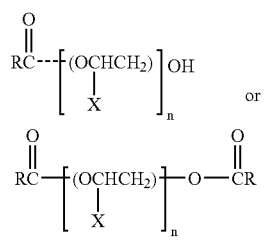

where RCO is the carboxylic ester radical, X is hydrogen or lower alkyl, and n is the number of polymerized alkoxy groups. In the case of the diesters, the two RCO-groups do not need to be identical. Preferably, R is a $C_{6-30}$ straight or branched chain, saturated or unsaturated alkyl, and n is from 1–100.

Also suitable are various types of alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

Anionic Surfactants

If desired the oxidative dye composition may contain one or more anionic surfactants. Together with the soap formed by the reaction of the fatty acid and alkanolamine or metal hydroxide, the ingredients provide the composition with the characteristics of shampoo. Preferred ranges of anionic surfactant are about 0.1–25%, preferably 0.5–20%, more preferably 1–15% by weight of the total composition. Suitable anionic surfactants include alkyl and alkyl ether sulfates generally having the formula $ROSO_3M$ and $RO(C_2H_4O)_x SO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula:

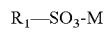

$$R_1\text{—}SO_3\text{-}M$$

wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide. The fatty acids may be derived from coconut oil, for example.

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula:

$$R_1-\overset{O}{\underset{\|}{C}}-\overset{R_2}{\underset{|}{N}}-(R_3)_n-COOM$$

wherein $R_1$ is a $C_{8-24}$ alkyl or alkenyl radical, preferably $C_{10-18}$; $R_2$ is H, $C_{1-4}$ alkyl, phenyl, or —$CH_2COOM$; $R_3$ is $CX_{2-}$ or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

Also suitable are amphoteric and zwitterionic surfactants. Examples of amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

(iv) Thickening Agents

Preferably the oxidative dye composition contains one or more thickening agents that increase the viscosity of the composition such that when it is applied to hair it doesn't run. The amount of thickening agent, if present, ranges from about 0.001–5%, preferably about 0.005–4%, more preferably about 0.005–3% by weight of the total composition.

A variety of thickening agents are suitable including low melting point waxes, carboxyvinyl polymers, and the like. Particularly preferred thickening agents are low melting point waxes such as emulsifying wax, fatty alcohols (e.g. stearyl alcohol, cetearyl alcohol, behenyl alcohol, and the like. Preferred are cetearyl alcohol and emulsifying wax.

(v) Solvents

It may be desirable to include one or more solvents in the dye composition. Such solvents assist in solubilizing the primary intermediate dyestuff and coupler dyestuff components, in addition to the other ingredients in the composition. The solvent is preferably present at about 0.01–10%, preferably 0.05–8%, more preferably 0.1–7% by weight of the total composition. Suitable solvents include $C_{2-4}$ alkanols such as ethanol, isopropanol, propanol, etc., as well as askoxydiglycols such as ethoxydiglycol. The preferred solvent comprises ethoxydiglycol.

(vi) Chelating Agents

Preferably, the oxidative dye composition contains one or more chelating agents that are capable of chelating the metal ions found in water. If water contains too many extraneous metal ions they can interfere with the coloration process. Preferred ranges of chelating agent are 0.001–5%, preferably 0.005–4%, more preferably 0.01–3% by weight of the total composition. Preferred chelating agents are EDTA, HEDTA, and sodium or potassium salts thereof.

(vii) Antioxidants and Preservatives

The oxidative dye composition may also contain one or more antioxidants such as BHA, BHT, sodium sulfite, and so on. Suggested ranges are from about 0.001–5%, preferably 0.005–4%, more preferably about 0.01–3% by weight of the total oxidative dye composition. Preservatives may also be incorporated into the oxidative dye composition.

2. The Developer Composition

In the claimed method, the oxidative dye composition is mixed with the developer to activate the dye composition so that it is suitable to color the hair. The developer composition, in its simplest form, is an aqueous solution of hydrogen peroxide. Preferably the developer composition comprises 1–99%, preferably 10–99%, more preferably 60–97% of water, and about 5–20%, preferably 6–15%, more preferably 7–10% by weight of the total developer composition of hydrogen peroxide. Developer compositions are generally sold in the form of 10, 20, 25, and 30 volume hydrogen peroxide. The 25 volume hydrogen peroxide developer composition contains about 7.5% by weight of the total composition of hydrogen peroxide. The 30 volume hydrogen peroxide developer composition contains about 9% by weight of the total composition of hydrogen peroxide. If desired, the developer composition may contain a variety of other ingredients that enhance the aesthetic properties and contribute to more efficient coloring of hair. Preferred developer compositions comprise:

0.5–25% hydrogen peroxide,
0.1–10% of a conditioner,
0.01–5% of a thickener, and
1–99% water.

(a). Conditioners

The developer composition may contain one or more conditioners that exert a conditioning effect on hair. The conditioners mentioned above for use in the oxidative dye compositions are also suitable for use in the developer composition, and in the same suggested ranges. Also suitable are various types of cationic silicones.

Cationic Silicones

As used herein, the term "cationic silicone" means any silicone polymer or oligomer having a silicon backbone, including polysiloxanes, having a positive charge on the silicone structure itself. Cationic silicones that may be used in the compositions of the invention include those corresponding to the following formula, where the ratio of D to T units, if present, are greater than about 80 D units to 1 T unit:

$$(R)_a\text{-}G_{3-a}\text{-Si}-(OSiG_2)_n-(OSiG_b(R_1)_{2-6b})_m O\text{—}SiG_{3-a}(R_1)_a$$

in which G is selected from the group consisting of H, phenyl, OH, $C_{1-10}$ alkyl, and is preferably $CH_3$; and a is 0 or an integer from 1 to 3, and is preferably 0; b is 0 or 1, preferably 1; the sum n+m is a number from 1 to 2,000 and is preferably 50 to 150; n is a number from 0 to 2000, and is preferably 50 to 150; and m is an integer from 1 to 2000, and is preferably 1 to 10; R is a $C_{1-10}$ alkyl, and $R_1$ is a monovalent radical of the formula $C_qH_{2q}L$ in which q is an integer from n2 to 8 and L is selected from the groups:

$$-N(R_2)CH_2-CH_2-N(R_2)_3{}^+A^-$$
$$-N(R_2)_3A^-$$
$$-N(R_2)_2CH_2-CH_2-NR_2C(R_2)_3A^-$$

in which $R_2$ is selected from the group consisting of H, phenyl, benzyl, a saturated hydrocarbon radical, and is preferably an alkyl radical containing 1–20 carbon atoms; and A- is a halide, methylsulfate, or tosylate ion.

(b). Thickeners

The developer composition may contain one or more thickeners that assist in maintaining an increased viscosity of the final composition resulting from mixture of the hair dye and the developer compositions. This ensures that the mixture is of a sufficient viscosity to prevent it from dripping or running off the hair onto the user's face or the surrounding environment. Suitable thickeners are those set forth in Section 4(e) above and in the same ranges. Also suitable are a variety of water soluble anionic thickening polymers such as those disclosed in U.S. Pat. No. 4,240,450, which is hereby incorporated by reference. Suggested ranges of such polymers are about 0.01–5%, preferably 0.05–4%, more preferably 0. 1–3% by weight of the total developer composition. Examples of such anionic polymers are copolymers of vinyl acetate and crotonic acid, graft copolymers of vinyl esters or acrylic or methacrylic acid esters, crosslinked graft copolymers resulting from the polymerization of at least one monomer of the ionic type, at least one monomer of the nonionic type, polyethylene glycol, and a crosslinking agent, and the like. Preferred are acrylate copolymers such as steareth-10 allyl ether acrylate copolymer.

(c). Other Ingredients

Nonionic Surfactants

The developer composition may contain one or more nonionic surfactants which assist in maintaining the composition in stable emulsion form. Suitable nonionic surfactants are the same as those mentioned above for use in the oxidative dye composition, and in the same amounts.

Chelating Agents

The developer composition may contain one or more chelating agents as described herein with respect to the dye composition, and in the same ranges by weight.

The oxidative dye composition and the developer composition are combined immediately prior to use to form a mixture that is applied to hair. The oxidative dye composition and the developer composition may be combined in any proportions so long as the mixture is capable of imparting color to hair in about 5 to 60 minutes, preferably about 10–40 minutes.

In the preferred embodiment of the invention, about 1 part of the oxidative dye composition is combined with 1.5 parts of the developer composition to form an aqueous based mixture. This combination is then immediately applied to hair and allowed to remain for twelve, preferably ten minutes. After ten minutes the hair is rinsed thoroughly with water.

B. Removing the Oxidative Dye Composition

The mixture applied to the hair above, is then rinsed from the hair with water after the desired period of time. The resulting hair has been colored or lightened, but it will be noted that the hair color may be somewhat monochromatic in nature. The hair is rinsed with water to remove the excess composition, but is not rinsed for so long a period as to leave no residual oxidizing agent on the hair fibers. Generally, the amount of rinsing that will remove the hair color mixture but not remove all of the residual oxidizing agent ranges from about 1 second to 5 minutes of water rinsing.

C. Treating Hair with the Post-Treatment Composition

After the hair has been rinsed with water to remove the hair color mixture, the hair is treated with a post-treatment composition, which is preferably in the shampoo form. The post-treatment composition is applied to the hair and allowed to remain for the desired period of time, generally ranging from about 15 seconds to five minutes, preferably about 30 seconds to 3 minutes.

1. Post-Treatment Composition

In its simplest form, the post treatment composition comprises one or more dyestuff components in an aqueous base. Preferably, the post-treatment composition comprises from about 0.001–15%, preferably about 0.005–10%, more preferably about 0.01–8% by weight of the total post-treatment composition of one or more dyestuff components, and about 0.001–99%, preferably about 0.005–98%, more preferably about 0.01–97% by weight of the total composition of water. The ingredients that may be found in the post-treatment composition are further described herein.

(a) Dyestuff Components

The post-treatment composition generally comprises one or more dyestuff components that are capable of coloring hair in the presence of an oxidizing agent. Such dyestuff components are the primary intermediates and couplers mention above, with respect to the oxidative dye composition. While the post-treatment composition contains dyestuff components, it is free of any oxidizing agents or other agents that are reactive with the dyestuff components to form color on the hair. Thus, the dyestuff components that are in the post-treatment composition will react with the residual oxidizing agent present on the hair fibers only. The rinsing of the hair fibers with water to remove the hair color mixture removes the oxidizing agent from the hair in a variable manner depending on factors such as hair porosity, damage, dye load, time of rinsing, and so on. Accordingly, the rinsed hair fibers will carry an uneven distribution of residual oxidizing agent. When the dyestuff components present in the post-treatment composition react with the uneven distribution of residual oxidizing agent present on the hair fibers, the result is an uneven, hence very natural, distribution of additional color, which provides both dimensionality and a highlight effect.

More importantly, when the post-treatment composition is in the shampoo form, it removes the excess, unreacted dye that is deposited on the outer surface of the hair cuticle and the unreacted dyestuff components in the shampoo composition react with the excess oxidizing agent on the hair to deposit more color in the hair.

One other notable feature of the post-treatment composition is that, while it contains dyestuff components, the dyestuff components do not provide color to the composition. In fact, unless other colorants are added, the post-treatment composition containing the dyestuff components tends to be clear. This is because the dyestuff components themselves are not capable of forming color unless activated by an activating agent such as a developer or similar type of oxidizing agent composition. Accordingly, the dyestuff components present in the-post-treatment composition have no effect unless and until they are contacted by some type of oxidizing agent as found in residual amounts on the rinsed hair fibers.

(b) Other Ingredients

The post-treatment composition may also contain a variety of other ingredients, in particular, any of those mentioned for use with the oxidative dye composition and in the same percentage ranges. Preferably, the post-treatment composition additionally comprises one or more surfactants, particularly anionic, betaine, or nonionic surfactants; one or more thickening agents; one or more fatty acids; and the like. Particularly preferred post-treatment compositions comprise by weight of the total post-treatment composition:

0.001–15% dyestuff components,
0.1–40% surfactants,
0.001–10% thickening agents.

Preferably the surfactants are anionic or betaine and are present in the ranges set forth above for the oxidative dye composition. Preferably the thickening agents that are present are in the same amounts as set forth above with respect to the oxidative dye composition. More preferred post-treatment compositions have a pH ranging from about 9 to 11 and a viscosity ranging from about 1,000 to 50,000 centipoise at room temperature. Additionally such composition may contain about 0.001–10% fatty acid and about 0.01–20% of one or more alkanolamines and/or fatty acid amides.

After the hair has been treated with the post-treatment composition for the desired period of time, the hair is rinsed well with water. The resulting hair will exhibit a dimensionality in color not seen with standard oxidative dye procedures and composition.

D. Optional Post Treatments

It may be desired to treat the hair with one or more additional treatments such as hair conditioner, if desired. Treating the hair with hair conditioner will provide additional protection to the hair and the moisturizing and conditioning agents present in the conditioner will reduce any dryness or damage in the fibers. Any hair conditioner is suitable, including those set forth in U.S. Pat. No. 5,989,533, which is hereby incorporated by reference in its entirety.

II. The Kit

The invention is also directed to a hair color kit comprising a storage receptacle having contained therein a first container containing an composition optionally comprising a dyestuff component, a second container containing an oxidizing agent composition, and a third container containing a post-treatment composition comprising at least one dyestuff component but being free of any oxidizing agent reactive with said dyestuff component to form color.

The kit is depicted in FIG. 1, and the different components that may be found I the kit are illustrated in FIGS. 2–5.

FIG. 1 shows a container 1 in the box form for housing the various components found in the kit of the invention. The container 1 may be in a variety of forms, but is preferably in the form of a box made of cardboard or similar paper type products. The box form facilitates on shelf storage in stores and is also a good surface for printing colorful indicia such as brand names, model photographs, and the like. Contained in the container 1 are the various components set forth in FIGS. 2–4, and optionally the component of FIG. 5.

Figure 2:
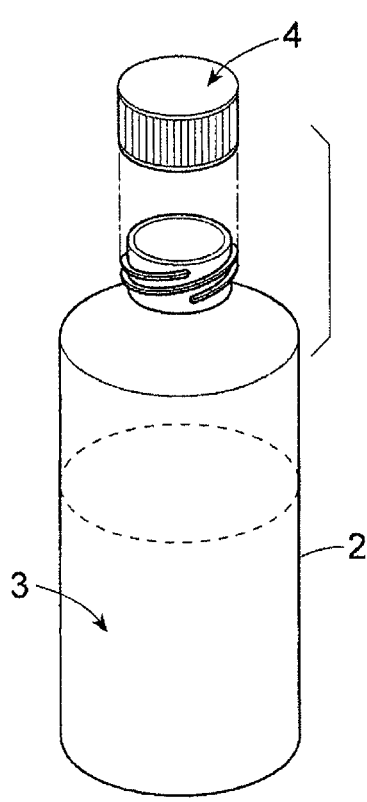
FIGS. 2–5 illustrate the various components that may be found in the kit.

FIG. 2 illustrates a bottle 2 for storage of the developer composition 3, the ingredients of which are described herein. The bottle 2 preferably has a removable cover 4.

Figure 3:
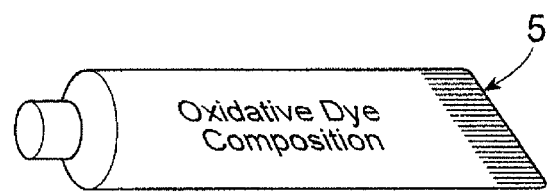

FIG. 3 illustrates oxidative dye composition 5 used in the method and kit of the invention. The ingredients that are found in the oxidative dye composition are set forth above. The oxidative dye composition 5 may be stored in a variety of containers, but a tube is preferred.

Figure 4:
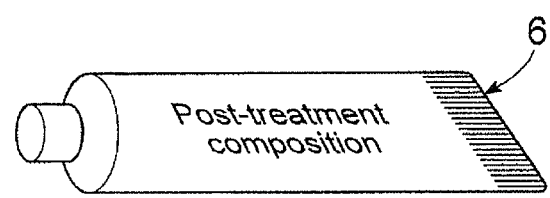

FIG. 4 illustrates the post-treatment composition 6 that is used in the method of the invention. The post-treatment composition 6 is preferably stored in a tube, but a variety of other containers are also suitable.

Figure 5:

FIG. 5 illustrates the optional hair conditioner composition 7 that may be included within the kit.

Figure 6:
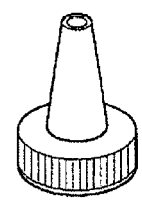
FIG. 6: illustrates an application nozzle for use in applying the hair color mixture.

FIG. 6 illustrates an application nozzle for use in applying the hair color mixture.

When the consumer desires to color her hair according to the method of the invention, the cover 4 of the bottle 2 containing the developer composition is removed. The oxidative dye composition 5 is added to the developer composition found in the bottle and either the cover 4 is replaced or the application nozzle of FIG. 6 is affixed. The consumer shakes the bottle 2 well to mix the contents. The contents of the bottle are applied to the hair using the application nozzle of FIG. 6. The mixture is left on the hair for the appropriate period of time and then removed by rinsing well with water. As mentioned above, the rinsing is conducted for a period of time sufficient to remove the mixture, but not so long as to completely remove all of the residual oxidizing agent that will be found on the hair fibers. Generally rinsing with water from about 0.5 to 4 minutes will accomplish the best results.

Thereafter, the post-treatment composition 6 is applied to the rinsed hair. The post-treatment composition 6, preferably in the form of a shampoo, is applied to the hair for a period of time ranging from about 15 seconds to 5 minutes, preferably about 1 to 2 minutes. The post-treatment composition is then rinsed from the hair well using water.

If desired, the kit may contain a hair conditioner composition. After removal of the post treatment composition from the hair, if desired, the hair conditioner is applied. The hair conditioner may be applied in one application or it may be desired to apply half of the hair conditioner after completion of the process, and the other half several weeks later. The dual application of hair conditioner keeps the hair moisturized and soft after the process, and adds additional moisture to the hair after several weeks.

The above mentioned process and kit provides dimensional hair color that looks very natural. In addition the color deposit is improved.

The invention will be further described in connection with the following examples which are set forth for the purposes of illustration only.

EXAMPLE 1

Oxidative dye compositions were prepared according to the following formula:

| Ingredient (% by weight) | A<br>Dark Blonde | B<br>Light Brown | C<br>Burgundy<br>Brown | D<br>Baby Blonde |
|---|---|---|---|---|
| Water | QS | QS | QS | QS |
| Erythrobic acid | 0.20 | 0.20 | 0.20 | 0.20 |
| Sodium sulfite | 0.50 | 0.50 | 0.50 | 0.50 |
| Ethoxydiglycol | 5.00 | 5.00 | 5.00 | 5.00 |
| Tetrasodium EDTA | 0.80 | 0.80 | 0.80 | 0.80 |
| Ethanolamine | 3.00 | 3.00 | 3.00 | 3.00 |
| Botanical extract | 0.80 | 0.80 | 0.80 | 0.80 |
| UV absorber* | 0.50 | 0.50 | 0.50 | 0.50 |
| Dark Blonde Dyestuff Components | 1.746 | — | — | — |
| Light Brown Dyestuff Components | — | 0.909 | — | — |
| Burgundy Brown Dyestuff Components | — | — | 3.35 | — |
| Baby Blonde Dyestuff Components | — | — | — | 0.02 |
| Ammonium lauryl sulfate (28% aqueous solution) | 2.00 | 2.00 | 2.00 | 2.0 |
| Oleic acid | 12.50 | 12.50 | 12.50 | 12.50 |

-continued

| Ingredient (% by weight) | A Dark Blonde | B Light Brown | C Burgundy Brown | D Baby Blonde |
|---|---|---|---|---|
| Cetearyl alcohol | 4.00 | 4.00 | 4.00 | 4.00 |
| Emulsifying wax | 2.00 | 2.00 | 2.00 | 2.00 |
| Oleth-20 | 1.00 | 1.00 | 1.00 | 1.00 |
| Steareth-21 | 0.70 | 0.70 | 0.70 | 0.70 |
| Meadowfoam seed oil | 0.75 | 0.75 | 0.75 | 0.75 |
| Oleyl alcohol | 0.40 | 0.40 | 0.40 | 0.40 |
| Polyquaternium 10 | 0.20 | 0.20 | 0.20 | 0.20 |
| Polyquaternium 28 | 0.50 | 0.50 | 0.50 | 0.50 |
| Mica/titanium dioxide (67:33) | 0.30 | 0.30 | 0.30 | 0.30 |
| Hydrolyzed wheat protein | 0.50 | 0.50 | 0.50 | 0.50 |
| Fragrance | 1.25 | 1.25 | 1.25 | 1.25 |
| Ammonium hydroxide (27.5%) | 9.00 | 9.00 | 9.00 | 9.00 |

*sodium benzotriazolyl butylphenol sulfonate

The compositions were prepared by combining all the ingredients except the ammonium hydroxide and fragrance mixing well to emulsify while heating to a temperature of about 25 to 80° C. The mixtures were then cooled to room temperature and the ammonium hydroxide and fragrance were added with mixing. The compositions were stored in tubes of laminated plastic and metal.

EXAMPLE 2

An oxidizing agent, or developer, composition was prepared according to the following formula:

| Ingredient | % by weight |
|---|---|
| Water | QS |
| Methyl paraben | 0.05 |
| EDTA | 0.02 |
| Mineral oil | 0.60 |
| Cetearyl alcohol/ceteareth-20 (80:20) | 4.00 |
| Lauramide MEA | 0.50 |
| Cyclomethicone/trimethylsiloxysilicate (50:50) | 0.01 |
| C12–16 pareth-9, trideceth-12, glycerin, water (20:6:4:2:3:65) | 2.00 |
| Hydrogen peroxide (35%) | 22.50 |
| Steareth-10 allyl ether/acrylates copolymer | 0.20 |
| Disodium phosphate | 0.03 |
| Phosphoric acid | 0.028 |

The composition was prepared by combining all ingredients and mixing well. The composition was stored in a plastic container.

EXAMPLE 3

Post-treatment compositions were prepared according to the following formulas:

| Ingredient (% by weight) | D Light Brown | E Burgundy |
|---|---|---|
| Water | QS | QS |
| Hydroxypropyl methylcellulose | 0.03 | 0.03 |
| Ethoxydiglycol | 2.00 | 2.00 |
| Erythrobic acid | 0.50 | 0.50 |
| Citric acid | 0.001 | 0.001 |
| Tetrasodium EDTA | 0.30 | 0.30 |
| Sodium sulfite | 0.50 | 0.50 |
| Brown Dyestuff Components | 2.90 | — |
| Burgundy Dyestuff Components | — | 5.00 |
| Sodium lauryl sulfate (30% aqueous solution) | 10.00 | 10.00 |
| Sodium laureth sulfate (28% aqueous solution) | 20.00 | 20.00 |
| Lauramide DEA (82–86% aqueous solution) | 2.00 | 2.00 |
| Cocamidopropyl betaine (35% aqueous solution) | 2.00 | 2.00 |
| Oleic acid | 6.00 | 6.00 |
| Ethanolamine | 2.00 | 2.00 |
| Fragrance oil | 0.75 | 0.75 |

The composition was prepared by combining all of the ingredients and mixing well. The resulting composition was clear and had a pH in the range of 9 to 10.

EXAMPLE 4

A hair conditioner composition was prepared according to the following formula:

| Ingredient | % by weight |
|---|---|
| Water | QS |
| Methyl paraben | 0.20 |
| Propyl paraben | 0.05 |
| Panthenol | 0.01 |
| Behentrimonium chloride | 4.00 |
| Glycerin | 5.00 |
| Cetearyl alcohol | 6.00 |
| Mango seed butter | 0.10 |
| Amodimethicone/trideceth-12/cetrimonium chloride (35% silicone) | 5.50 |
| Sodium benzotriazolyl butylphenol sulfonate, buteth-3, tributyl citrate | 0.005 |
| Fragrance | 0.50 |
| Cholesteryl oleyl carbonate, cholesteryl chloride, cholesteryl nonanoate | 0.01 |
| Isostearyl citrate/glycolate/lactate/malate | 0.01 |
| Citric acid | 0.022 |
| Methylchloroisothiazolinone, methylisothiazolinone | 0.04 |
| Polyethylene terephthalate, acrylates copolymer | 0.30 |

The above composition was made by combining the ingredients and mixing well.

EXAMPLE 5

Two swatches of 95% gray hair swatches weighing 1.5 grams each and two swatches of light brown virgin hair swatches weighing 1.5 grams each were used. Approximately 6 parts of the light brown dye composition of Example 1 was combined with 9 parts of the oxidizing agent composition of Example 2. This mixture was applied to each of the two gray and two brown swatches and allowed to remain for 10 minutes. All swatches were rinsed with water for 15 seconds. The hair conditioner composition of Example 4 was applied to one (originally) gray and one (originally) brown swatch for 2 minutes, then rinsed off with water. The other swatches were washed with shampoo composition E of Example 3 (burgundy post-treatment composition) for two minutes, then rinsed with water. The hair conditioner composition of Example 4 was then applied to these swatches for 2 minutes, then rinsed off with water. The swatches treated with burgundy post-treatment shampoo composition E of Example 3 showed significant red tones and dimensionality when compared with the swatches that were treated only with the hair conditioner composition.

EXAMPLE 6

Two 95% gray hair swatches weighing 1.5 grams each and two light brown virgin hair swatches weighing 1.5 grams each were used. Approximately 6 parts of the baby blonde dye composition D in Example 1 was combined with 9 parts of the oxidizing agent composition of Example 2 and applied to the swatches. The mixture was applied to each of the swatches and allowed to remain for 10 minutes. All swatches were rinsed with water for 15 seconds. One set of the swatches (one originally gray, one originally virgin brown) was treated with the hair conditioner composition of Example 4 for two minutes. The other swatches were treated with the shampoo composition E (burgundy post-treatment composition) of Example 3 for two minutes. After the post-treatment composition was rinsed from the hair with water, the hair conditioner composition of Example 4 was applied for 2 minutes, then rinsed off with water. The swatches treated with the burgundy post-treatment shampoo composition E of Example 3 showed significant red tones and dimensionality. The swatches that were treated only with the hair conditioner exhibited no red tones at all.

EXAMPLE 7

Three sets of three swatches, each of 95% gray hair, weighing 1.5 grams each, were used. Approximately 6 parts of the light brown dye composition of Example 1 was combined with 9 parts of the oxidizing agent composition of Example 2. The mixture was applied to each of the swatches and allowed to remain for 10 minutes. All swatches were rinsed with water for 15 seconds. The first set of three swatches was kept aside for the control (C*, below) and washed for 0, 4, and 28 shampoos. After each shampoo the hair conditioner of Example 4 was applied for two minutes, then rinsed off with water. The two other sets of swatches were treated as follows:

Set 2: This set of three swatches was treated with the light brown post-treatment composition D of Example 3 (TD* below), by shampooing the swatches for 2 minutes, then rinsing well with water. One of the swatches was kept as (0 wash), and the other two swatches were washed 4 and 28 times. After each shampoo, the hair conditioner of Example 4 was applied for 2 minutes, then rinsed off with water. The control and test swatches were measured by the datacolor color tools QC (version 1.2.1) spectrocolorimeter. The chromaticity (c*) of the swatches was measured from values of a*, b*, in the L*, a*, and b* international color notation system. The degree of lightening was determined from the change in L (lightening), a (red), and b (yellow) values. The results were as follows:

| C* | L | a | b | ΔL | ΔE | TD** | L | a | b | ΔL | ΔE |
|---|---|---|---|---|---|---|---|---|---|---|---|
| 0 | 35.00 | 3.86 | 9.10 | | | 0 | 33.11 | 4.41 | 11.01 | | |
| 4 | 38.05 | 4.06 | 10.06 | 3.05 | 3.20 | 4 | 35.78 | 4.15 | 11.13 | 2.67 | 2.67 |
| 28 | 38.41 | 3.89 | 9.31 | 3.40 | 3.41 | 28 | 35.64 | 4.01 | 9.84 | 2.54 | 2.80 |

C* = number of washes, control swatches

TD** = number of washes, test swatches treated with Composition D from Example 3, the brown post-treatment composition.

The above results illustrate that, in general, the method and compositions of the invention provide improved color deposit and fade resistance. In addition, the color change in the swatches treated with Composition D was apparent with visual inspection. The treated swatches exhibited a multi-dimensional appearance and the color of the swatches was significantly browner in tone than that of the control.

Set 3: This set of three swatches was treated with the Burgundy post treatment Composition E of Example 3 by shampooing the swatches for 2 minutes, then rinsing well with water. One swatch was kept aside (0 wash). The other two swatches were shampooed 4 and 28 times with Composition E. After each shampoo, the hair conditioner of Example 4 was applied for 2 minutes, then rinsed off with water. The control and test swatches were measured by the datacolor color tools QC (version 1.2.1) spectrocolorimeter. The results are as follows:

| C* | L | a | b | ΔL | ΔE | TE** | L | a | b | ΔL | ΔE |
|---|---|---|---|---|---|---|---|---|---|---|---|
| 0 | 35.00 | 3.86 | 9.10 | | | 0 | 22.29 | 8.65 | 4.11 | | |
| 4 | 38.05 | 4.06 | 10.06 | 3.05 | 3.20 | 4 | 27.72 | 8.56 | 6.67 | 5.43 | 6.00 |
| 28 | 38.41 | 3.89 | 9.31 | 3.40 | 3.41 | 28 | 27.90 | 9.30 | 6.36 | 5.61 | 6.08 |

C* = number of washes, control swatches.

TE** = number of washes, test swatches treated with composition E from Example 3.

The above results illustrate that when post treatment composition E is applied to the test swatches there is considerable color deposit, particularly in the red tones, even though composition E contains no oxidizing agent.

The color change in the swatches treated with Composition E also is also visually apparent, and exhibited a multi-dimensional appearance with red tones.

EXAMPLE 8

Two sets of three swatches each of 95% gray hair, each weighing 1.5 grams, were used. Approximately 6 parts of the dark blonde dye composition A of Example 1 was combined with 9 parts of the oxidizing agent composition of Example 2. The mixture was applied to each of the swatches and allowed to remain for 10 minutes. All swatches were rinsed with water for 15. seconds. The first set of swatches was kept aside for the control and washed 0, 4, and 28 shampoos. After each shampoo the hair conditioner of example 4 was applied for 2 minutes, then rinsed off with water. The second set of three swatches was treated with the light brown post-treatment composition D of Example 3 by shampooing the swatches for 2 minutes, then rinsing well with water. One swatch was kept aside (0 wash). The other swatches were washed 4 and 28 times with Composition D. After each shampoo, the hair conditioner composition of Example 4 was applied for 2 minutes, then rinsed off with water. The control and test swatches were measured by the datacolor color tools QC (version 1.2.1) spectrocolorimeter. The chromaticity (c*) of the swatches was measured from values of a*, b*, in the L*, a*, and b* international color notation system. The degree of lightening was determined from the change in L (lightening), a (red), and b (yellow) values. The results were as follows:

The above results illustrate that when the post treatment composition D is applied to the swatches, there is noticeable color deposit over and above the control even though the post treatment composition does not contain any oxidizing agent. Further, the swatches treated with the post treatment composition show less color wash out.

EXAMPLE 9

Three sets of three swatches, 95% gray hair, each weighing 1.5 grams, were used. Approximately 6 parts of the burgundy brown dye composition C of Example 1 was combined with 9 parts of the oxidizing agent composition of Example 2 and applied to the swatches. The mixture was applied to each of the swatches and allowed to remain for 10 minutes. All swatches were rinsed with water for 15 seconds. The first set of swatches was kept aside for the control and washed for 0, 4, and 28 shampoos. After each shampoo the hair conditioner of example 4 was applied for 2 minutes, then rinsed off with water. The second set of swatches were treated with the burgundy post-treatment composition E of Example 3 by shampooing the swatches for 2 minutes, then rinsing well with water. One swatch represented 0 wash, and the other two swatches were washed 4 and 28 times with Composition E. After each shampoo the hair conditioner of example 4 was applied for 2 minutes, then rinsed off with water. The control and test swatches were measured by the datacolor color tools QC (version 1.2. 1) spectrocolorimeter. The chromaticity (c*) of the swatches was measured from values of a*, b*, in the L*, a*, and b* international color notation system. The degree of lightening was determined from the change in L (lightening), a (red), and b (yellow) values. The results were as follows:

| C* | L | a | b | ΔL | ΔE | TD** | L | a | b | ΔL | ΔE |
|---|---|---|---|---|---|---|---|---|---|---|---|
| 0 | 39.98 | 6.00 | 14.65 | | | 0 | 34.52 | 5.97 | 13.20 | | |
| 4 | 42.10 | 6.22 | 15.93 | 2.13 | 2.49 | 4 | 35.59 | 6.30 | 13.29 | 1.07 | 1.12 |
| 28 | 42.92 | 5.68 | 14.95 | 2.94 | 2.98 | 28 | 35.04 | 6.07 | 12.23 | 0.52 | 1.11 |

C* = number of washes, control swatches

TD** = number of washes, test swatches treated with Composition D from Example 3.

| C* | L | a | b | ΔL | ΔE | TE** | L | a | b | ΔL | ΔE |
|---|---|---|---|---|---|---|---|---|---|---|---|
| 0 | 27.02 | 12.22 | 6.66 | | | 0 | 23.53 | 11.85 | 5.40 | | |
| 4 | 28.35 | 12.87 | 7.53 | 1.33 | 1.71 | 4 | 23.38 | 11.88 | 5.09 | −0.15 | 0.34 |
| 28 | 28.97 | 12.72 | 7.75 | 1.95 | 2.29 | 28 | 25.02 | 12.39 | 5.80 | 1.49 | 1.64 |

C* = number of washes, control swatches
TE** = number of washes, test swatches treated with Composition E from Example 3.

The above results illustrate that when the post treatment composition E is applied to the swatches, there is noticeable color deposit over and above the control with more red tones, even though the post treatment composition does not contain any oxidizing agent. Further, the swatches treated with the post treatment composition show less color wash out when compared to the control.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A method for oxidatively coloring the hair comprising the steps of:
   (a) treating the hair with an oxidative dye composition comprising at least one oxidative dyestuff component and at least one oxidizing agent reactive with the oxidative dyestuff component to form color, for a period of time sufficient to color the hair,
   (b) removing the oxidative dye composition from the hair but leaving residual oxidizing agent on at least portion thereof,
   (c) treating the hair with a post-treatment composition comprising at least one oxidative dyestuff component but being free of any oxidizing agent reactive with said dyestuff component to form color, whereby the oxidative dyestuff component in the post-treatment composition reacts with any residual oxidizing agent present on the hair to form color.

2. The method of claim 1 wherein the oxidative dyestuff component in the oxidative dye composition comprises at least one primary intermediate and, optionally, at least one coupler for the formation of oxidation dyes.

3. The method of claim 2 wherein the oxidative dyestuff component in the post-treatment composition comprises at least one primary intermediate and, optionally, at least one coupler for the formation of oxidation dyes.

4. The method of claim 3 wherein the oxidative dye composition comprises, by weight of the total composition, about 0.01–99.9% water, and about 0.01–99% oxidative dyestuff component.

5. The method of claim 4 wherein the post-treatment composition comprises about 0.01–99.9% water and about 0.01–99.9% oxidative dyestuff component.

6. The method of claim 5 wherein the post-treatment composition further comprises a surfactant.

7. The method of claim 6 wherein the surfactant is an anionic, cationic, nonionic, zwitterionic, or amphoteric surfactant.

8. The method of claim 7 wherein the surfactant comprises an anionic surfactant.

9. The method of claim 8 wherein the anionic surfactant is an alkyl sulfate, an alkyl ether sulfate, or mixtures thereof.

10. The method of claim 1 wherein the hair treated with the post-treatment composition was oxidatively dyed with an oxidative dye composition containing (i) a dyestuff component comprising at least one primary intermediate and, optionally, at least one coupler for the formation of oxidation dyes; and (ii) at least one oxidizing agent reactive with the dyestuff component to form color.

11. The method of claim 1 wherein the post-treatment composition contains an oxidative dyestuff component comprising at least one primary intermediate and, optionally, at least one coupler for the formation of oxidation dyes.

12. The method of claim 1 wherein the oxidative dyestuff component in the oxidative dye composition contains at least one primary intermediate that is the same as a primary intermediate in the dyestuff component in the post-treatment composition.

13. The method of claim 1 wherein the oxidative dyestuff component in the oxidative dye composition contains at least one primary intermediate or coupler that is different from at least one primary intermediate or coupler in the oxidative dyestuff component of the post-treatment composition.

14. The method of claim 8 wherein the post-treatment composition further comprises a solvent.

15. The method of claim 14 wherein the solvent comprises one or more mono-, di-, or polyhydric alcohols.

16. The method of claim 14 wherein the solvent comprises a glycol.

17. The method of claim 1 wherein the hair was oxidatively colored in ten minutes or less.

18. The method of claim 1 wherein the oxidative dye composition colors the hair one color and the post-treatment composition colors the hair having residual oxidizing agent thereon a different color.

19. The method of claim 1 wherein the oxidative dye composition is removed from the hair by rinsing with water.

20. The method of claim 19 wherein the hair is rinsed with water for about 1 second to 5 minutes.

21. The method of claim 18 wherein the oxidizing agent composition comprises hydrogen peroxide.

22. The method of claim 5 wherein the post-treatment composition comprises about 0.01–99% water, about 0.0001–25% oxidative dyestuff component, about 0.001–25% surfactant, and about 0.001–20% solvent.

23. The method of claim 22 wherein the oxidative dyestuff component comprises about 0.0001–20% of at least one primary intermediate and about 0.0001–15% of at least one coupler for the formation of oxidation dyes.

24. The method of claim 1 wherein the post-treatment composition contains oxidative dyestuff components that are color matched to the oxidative dyestuff components used to oxidatively color the hair.

* * * * *